(12) United States Patent
Girke et al.

(10) Patent No.: US 6,464,631 B1
(45) Date of Patent: Oct. 15, 2002

(54) ENDOSCOPE WITH A DISTAL VIDEO CAMERA AND A CAMERA ROTATING DEVICE

(75) Inventors: Olaf Girke, Hamburg (DE); Andreas Mückner, Berlin (DE)

(73) Assignee: Olympus Winter & Ibe GmbH, Hamburg (DE)

( * ) Notice: Subject to any disclaimer, the term of this patent is extended or adjusted under 35 U.S.C. 154(b) by 0 days.

(21) Appl. No.: 09/715,682

(22) Filed: Nov. 16, 2000

(30) Foreign Application Priority Data

Nov. 17, 1999 (DE) .......................... 199 55 229

(51) Int. Cl.⁷ ................................. A61B 1/05
(52) U.S. Cl. .................. 600/109; 600/137; 600/173
(58) Field of Search .................. 600/109, 137, 600/173, 160; 348/65, 85

(56) References Cited

U.S. PATENT DOCUMENTS

| 4,858,001 A | 8/1989 | Milbank et al. |
| 4,936,307 A | 6/1990 | Saito et al. |
| 5,588,948 A | 12/1996 | Takahashi et al. |
| 6,097,423 A | * 8/2000 | Mattson-Boze et al. ...... 348/65 |

FOREIGN PATENT DOCUMENTS

| DE | 39 39 417 C1 | 12/1990 | |
| EP | 0 845 694 A1 | 6/1998 | |
| JP | 60-196719 | 10/1985 | |
| JP | 60-241018 | 11/1985 | |
| JP | 06-269406 | * 9/1994 | ............ A61B/1/04 |
| JP | 10-192233 | * 7/1998 | ............ A61B/1/04 |
| JP | 2000-180735 | * 6/2000 | ............ A61B/1/00 |

* cited by examiner

Primary Examiner—John Mulcahy
(74) Attorney, Agent, or Firm—Rankin, Hill, Porter & Clark LLP

(57) ABSTRACT

An endoscope having a distal tubular shaft section of smaller diameter in which at least on longitudinally-extending device, such as a light guiding fiber bundle, is arranged. An objective and a video camera are disposed in a free cross-sectional area of the tubular shaft section. The video camera is arranged for rotation about its viewing direction by a rotation device. An electric motor is arranged proximally of the video camera in the free cross-sectional area. The electric motor is connected to the video camera with the motor drive shaft being disposed parallel to the axis of the tubular shaft section.

3 Claims, 3 Drawing Sheets

ENDOSCOPE WITH A DISTAL VIDEO CAMERA AND A CAMERA ROTATING DEVICE

Figure 1:
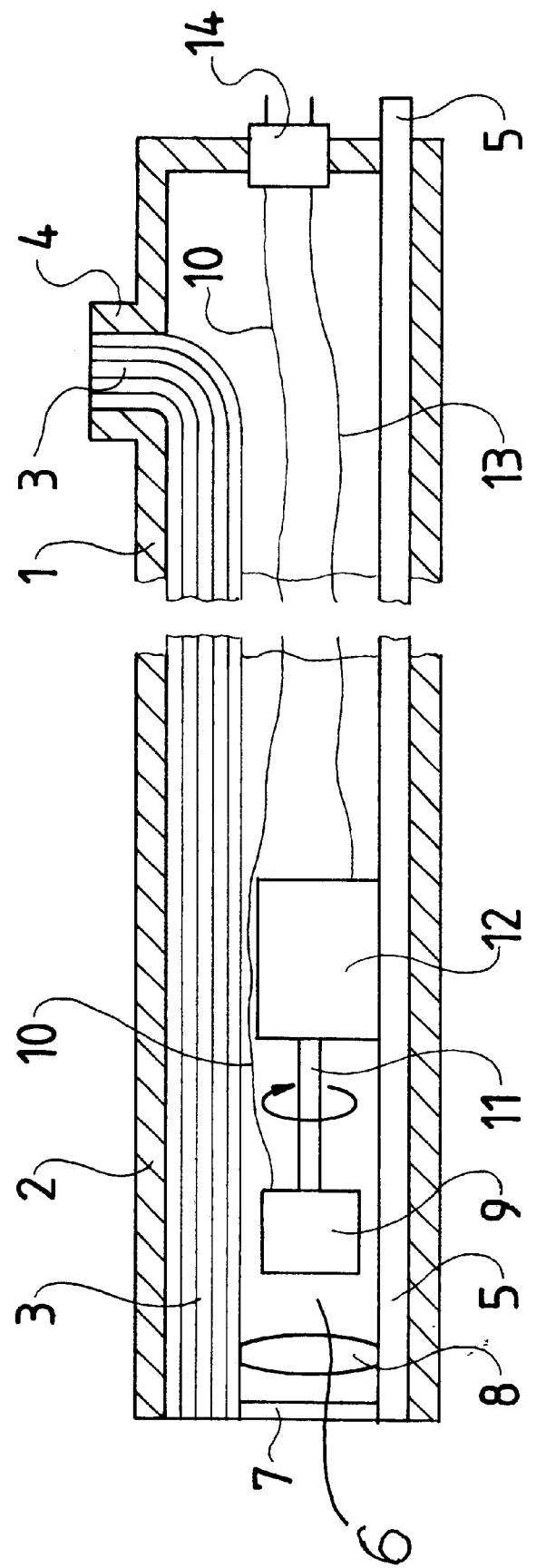

The invention relates to an endoscope of the type referred to in the preamble of Claim 1.

Older endoscope constructions have an image guide, e.g. in the form of a rod lens optical system, between the distally arranged objective and a proximally arranged ocular. Viewing is effected with the eye at the ocular. The endoscope can be rotated at will without viewing being influenced.

Video viewing is becoming increasingly prevalent nowadays. The endoscope is provided with a video camera. Viewing is effected on a monitor, which is installed separately. If the video camera is rigidly connected to the endoscope and if the endoscope is rotated, the image rotates on the monitor which results in considerable irritation of the observer.

Constructions are known in the prior art in which the video camera is arranged proximally on an endoscope with an image guide and is arranged, for instance, freely rotatably hanging there in order to ensure the upright position of the image when the endoscope is rotated. Constructions are also known in which the proximally arranged video camera is rotated with a motor. In order to ensure the upright position of the image, the rotation of the camera can be effected e.g. in dependence on sensors installed in the endoscope which monitor its rotational position and enable control whereby the image is always maintained upright by appropriate rotation of the camera.

In endoscopes of the type referred to above, as are known from U.S. Pat. No. 4,858,001, the video camera is arranged distally directly at the objective in order to economise on an image guide. The problem of rotation of the video camera is solved in this known construction also by a shaft, which carries the video camera and extends through the entire length of the tubular shaft and which is coupled to a rotary actuator in the main body located proximally of the tubular shaft. This construction has, however, disadvantages. The shaft, which extends through the tubular shaft and is connected to a proximal rotary actuator, results in sealing problems. These are very difficult to solve, particularly in the case of medical endoscopes which must be autoclaved in hot steam. If steam enters the endoscope, water condensation on the objective and the video camera results in the endoscope becoming unusable. Furthermore, the shaft takes up a great deal of space in the otherwise free internal cross-section of the tubular shaft, which could be used in other ways.

The object of the present invention resides in providing an endoscope of the type referred to above which may be better sealed and renders a better utilisation of the free cross-sectional area in the tubular shaft possible.

This object is solved in accordance with the invention with the features of Claim 1.

In accordance with the invention, arranged in the free cross-sectional area of the distal tubular shaft section, which remains there after positioning the longitudinally extending devices, particularly such as the conventional light guiding fibre bundle or other devices, such as working passages, flushing passages and the like, proximally of the video camera there is an electric motor which rotates the latter. This structural unit comprising an optical system and a video camera, and optionally includes the motor, which is inherently spatially sealed, can be encapsulated in a vapour-tight manner in order to protect the objective and the video camera from steam, whereby only the signal lines, control lines and power supply lines for the video camera and the motor need pass out to the exterior in a conventional and well understood technique. The free cross-sectional area of the tubular shaft proximally of the electric motor remains free and can be used for other purposes.

The vapour-tight encapsulation is preferably effected with the features of Claim 2. The motor can be disposed outside the inner tube, which encloses only the objective and camera, whereby, however, a sealed rotary bushing would be necessary. The features of Claim 3 are therefore advantageously provided, which results in an encapsulation through which only electric lines pass in a sealed manner.

The inner tube for the vapour-tight encapsulation of the video camera is positioned with a small cross-sectional area in the free cross-sectional area of the tubular shaft. Bushings for electrical lines provided on it must be vapour-tight and cannot be made smaller to an unlimited extent. If the power supply lines for the motor must also pass through them, space problems arise. The features of Claim 4 are therefore advantageously provided. In this construction, the inner tube is made of magnetically permeable material, e.g. high-grade steel and extends through the gap in the motor. The stator thereof is thus located outside the inner tube. With suitable motor constructions an electrical connection is necessary only on the stator which consequently can be positioned outside the inner tube without a special vapour-tight bushing. The inner tube thus requires only bushings for the lines of the video camera. Since the inner tube has a smaller diameter in the vicinity of the motor than at the position of the video camera, the external diameter of the stator of the motor can correspond to the external diameter of the inner tube in the vicinity of the video camera so that it fits into the free cross-sectional area of the tubular shaft section.

Figure 2:
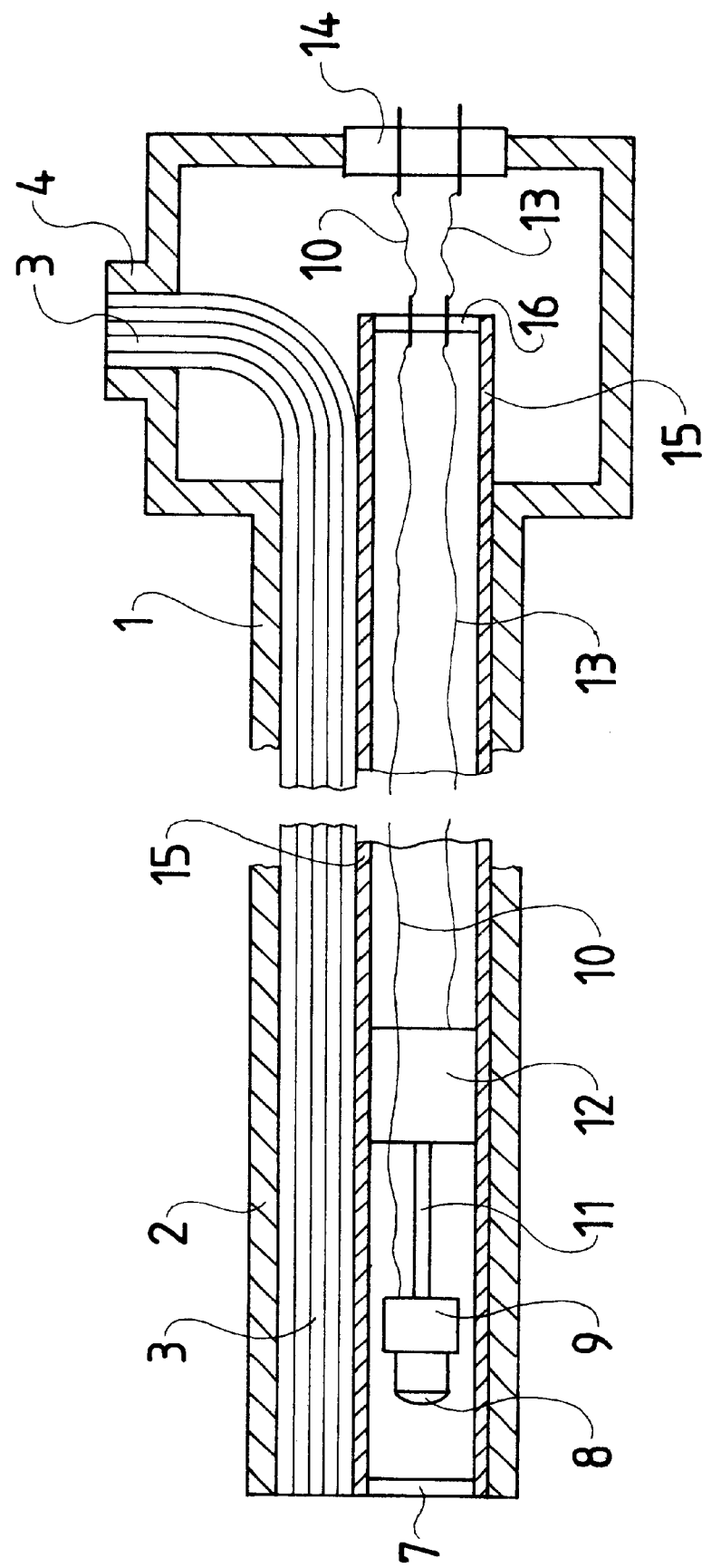
Figure 3:
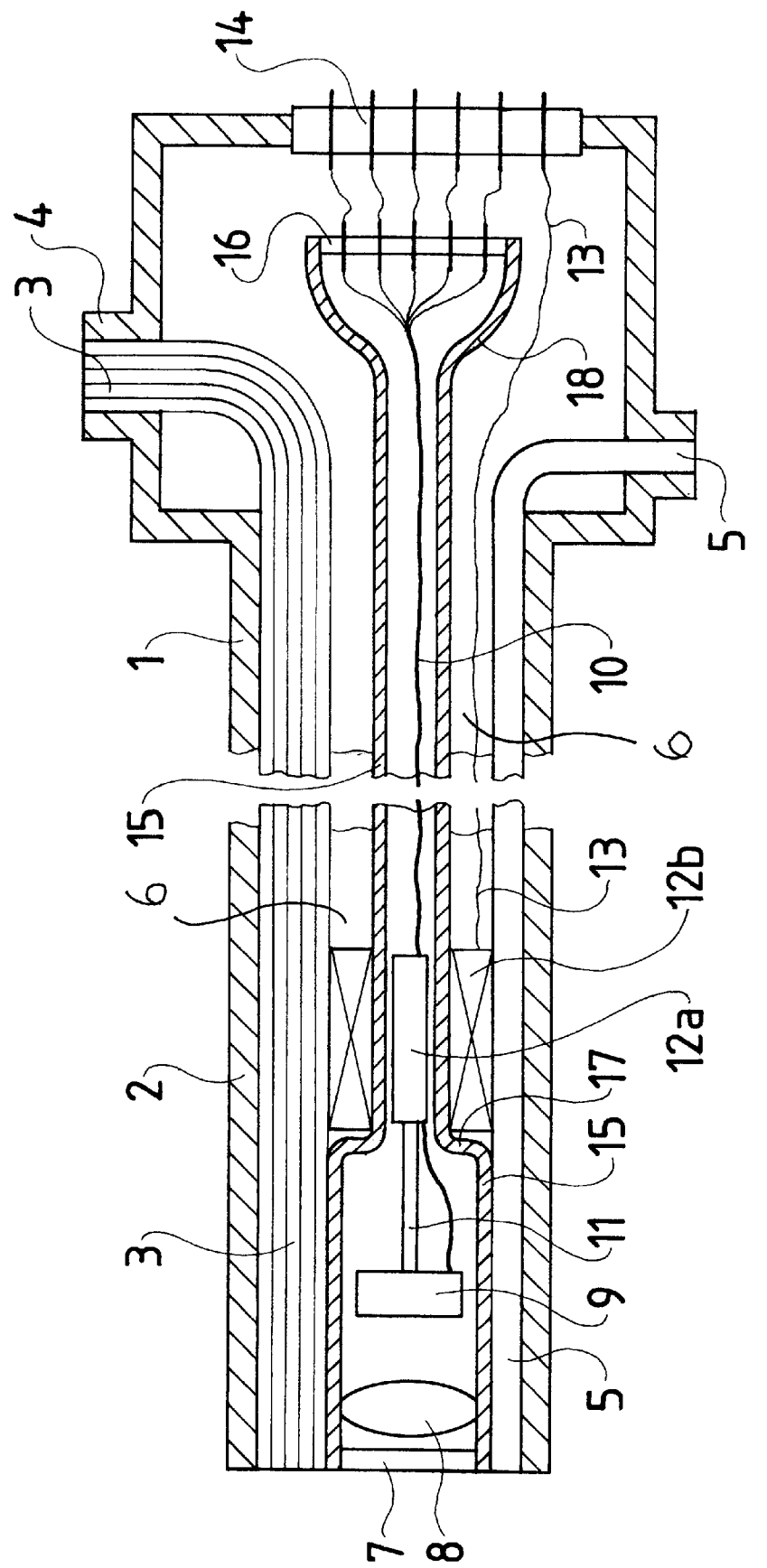

The invention is illustrated schematically and by way of example in the drawings, in which:

FIG. 1 is a longitudinal sectional view of an endoscope in accordance with a first embodiment of the invention, FIG. 2 is a longitudinal sectional view of an endoscope in accordance with a second embodiment of the invention and FIG. 3 is a longitudinal sectional view of an endoscope in accordance with a third embodiment of the invention.

FIG. 1 is a highly schematic longitudinal sectional view of a first embodiment of an endoscope in accordance with the invention. The endoscope has a tubular shaft 1 with a distal tubular shaft section 2 and two devices extend through its entire length. One of these is a light guiding fibre bundle 3, which terminates in the distal end surface of the endoscope and terminates proximally in a connecting socket 4, which extends laterally away from the proximal region of the tubular shaft 1. A further device, which extends longitudinally through the tubular shaft 1, is shown, by way of example, in the form of a working passage 5, which extends straight through the entire endoscope and is used e.g. for the introduction of instruments, gases or liquids.

The devices which extend through longitudinally in the form of the light guiding fibre bundle 3 and the working passage 5 leave a free cross-sectional area 6 in the tubular shaft 1, and particularly in its distal tubular shaft section 2, which is sealed at the distal end surface of the tubular shaft 1 with a window 7. Arranged proximally behind the latter in the free cross-sectional area 6 is an objective 8, which is indicated schematically, and behind that in the free cross-sectional area 6 is a freely rotatable video camera 9, which can comprise e.g. substantially an image conversion chip. This is connected to the exterior by means of a cable 10.

The video camera 9 is secured to a shaft 11, which is arranged parallel to the axis of the tubular shaft and constitutes the drive shaft of an electric motor 12 stationarily arranged in the free cross-sectional area 6. The electric motor is connected to the exterior by means of an electric cable 13. The two cables 10, 13 extend to the exterior proximally through the wall of the tubular shaft 1 via a sealed bushing 14.

If the illustrated endoscope is rotated with its tubular shaft 1, the video camera 9 can be returned by appropriate control of the motor 12 so that the image viewed on a monitor, which is not shown, remains upright. For this purpose, the signal from a position sensor which is not shown, can be, for instance, used, which can be arranged in the remaining free internal space in the tubular shaft 1. Rotation of the image produced by the video camera 9 can also be detected with an image evaluation device and a return control signal calculated therefrom.

The construction illustrated in simplified and highly schematic form in FIG. 1 has sealing problems. The light guiding fibre bundle 3 is densely packed and secured by adhesive or cement in its distal end region adjacent the window 7, but not in a vapour-tight manner. If the endoscope is used for medical applications and sterilised in hot steam under high pressure, steam can enter at this point. After cooling, moisture condenses on the objective lens 8 and on the video camera 9 so that the instrument becomes unusable.

For the purpose of better sealing, the window 7 could be extended in front of the distal end surface of the light guiding fibre bundle 3 over the entire internal area of the tubular shaft 1 and a well sealed, e.g. soldered, window could also be provided at the proximal end of the light guiding fibre bundle 3 in the connecting socket 4. Such a construction results, however, in other problems, particularly in back-reflection of light in the window from the distal end surface of the light guiding fibre bundle 3 to the objective 8.

These sealing problems are solved with the modified construction illustrated in FIG. 2 in which the same reference numerals have been used as in FIG. 1, insofar as this is possible.

In distinction to FIG. 1, the tubular shaft 1 in this case is shown firstly broadened in its proximal end region to form a main body. The light guide 3 is positioned in the same manner as in the embodiment of FIG. 1. An inner tube 15 is, however, provided which is sealed at its distal end with a window 7 and which encloses the motor 12, the shaft 11, the video camera 9 and the objective 8 in its interior. In the illustrated exemplary embodiment, the internal tube 15 terminates proximally in the broadened main body region of the tubular shaft 1 and is provided at that position with a bushing 16 for the cables 10 and 13, which can be constructed in an optimally sealed manner, e.g. in the form of a fused glass seal. The outer cable bushing 14, which corresponds to the bushing illustrated in FIG. 1, on the other hand need have only a relatively small sealing action.

The inner tube 15 with the aforementioned bushing 16 constituted by a fused glass seal and an e.g. soldered in window 7 can be constructed to be extremely gas-tight.

FIG. 2 shows that the objective 8 can also be arranged directly on the video camera 9 so as to rotate with it, though the fixed arrangement of the objective illustrated in FIG. 1 would also be possible in this case.

Further devices extending longitudinally through the tubular shaft 1 are not provided in FIG. 2, although such devices, e.g. the working passage 5 illustrated in FIG. 1 outside the inner tube 15 can be provided in this construction also. The sealing problems resulting with such further devices in the construction of FIG. 2 are not disruptive.

FIG. 3 shows a modification of the construction of FIG. 2 which is again provided with the same reference numerals, where possible.

The tubular shaft 1 with its distal tubular shaft section 2 corresponds substantially to the construction of FIG. 2. The light guiding fibre bundle 3 is also provided in the same manner.

An inner tube 15 is again provided, which is provided distally with a well sealed, e.g. soldered in, window 7 and accommodates the objective 8 and the video camera 9, which is rotated by means of the shaft 11. The objective 8 is fixedly arranged in the inner tube 15 in FIG. 3 but could also be arranged on the camera 9 so as to rotate with it, as in the embodiment of FIG. 2.

In its distal section accommodating the window 7, the objective 8 and camera 9, the inner tube 15 has a diameter corresponding to the embodiment of FIG. 2 and thus fills the free cross-sectional area at this point of the distal shaft section which remains after positioning the light guiding fibre bundle 3 and further longitudinally extending devices, which also includes e.g. the working passage 5, which is shown positioned outside the inner tube 15 in the exemplary embodiment of FIG. 3.

Proximally of the camera 9, in the vicinity of the shaft 11, the inner tube 15 narrows at the point 17 and extends from there in the proximal direction with a smaller diameter. This smaller diameter extends through the electric motor whose important components, namely the rotor 12a, which drives the shaft 11, and the stator 12b are shown. The inner tube 15, which is constricted at this point, extends through the motor gap between the rotor 12a and stator 12b. A type of motor is used which requires electrical connections only on the stator 12b. The motor connecting cable 13 thus extends from there outside the inner tube 15 and without sealing problems to the outer bushing 14, which passes through the housing of the tubular shaft 1.

The video cable 10 extends within the inner tube 15 through the region of the motor 12a, 12b and can pass, e.g. for space reasons as illustrated, through the rotor 12a, which is constructed, for instance, in the form of a simple permanent magnet.

The video cable 10 passes through the well sealed bushing 16 at the proximal end of the inner tube 15. It is shown in FIG. 3 that the video cable 10 can comprise a plurality of lines which transmit the video signal, control data, the supply current and the like. A great deal of space is required with the very well sealed bushing 16, which is constructed e.g. in the form of a glass plate soldered into the inner tube 15 with metal pegs fused into it. The inner tube 15, which is of constricted diameter in the region of the motor 12a, 12b, is thus broadened towards the bushing 16 at the point 18, which is situated in the region of the tubular shaft 1 which is broadened to form a main body.

What is claimed is:

1. An endoscope with a distal tubular shaft (2) of small diameter, in which at least one longitudinally extending device (3, 5) in the form of a light guiding fiber bundle (3) is arranged, an objective (8) and a video camera (9) being arranged in a cross-sectional area (6) of the tubular shaft section (2) that is free of said at least one longitudinally extending device (3, 5), the video camera being arranged to be rotatable about its viewing direction by means of a rotation device (11, 12), wherein an electric motor (12) serves as the rotation device and is disposed proximally of the video camera (9) in the free cross-sectional area (6), said motor being secured to the video camera (9) with a drive shaft (11) of the motor being arranged parallel to an axis of the tubular shaft section (2), the objective (8) and the video camera being arranged in an inner tube (15) having a distal window (7), the inner tube being arranged in the free cross sectional area (6), and wherein the inner tube (15) comprises magnetically permeable material and has a smaller diameter in the region of the motor (12a, 12b) than at the video camera (9) and extends through a motor gap extending concentrically with the drive shaft (11) between an inner rotor (12a) and an outer stator (12b) of the motor.

2. The endoscope as claimed in claim 1, wherein the motor (12) is arranged in the inner tube (15).

3. The endoscope according to claim 1, wherein said drive shaft has a first end connected to said motor and a second, opposite end connected to said video camera.

* * * * *